United States Patent [19]

Müller et al.

[11] Patent Number: 4,836,203
[45] Date of Patent: Jun. 6, 1989

[54] DEVICE FOR THERAPEUTICAL IRRADIATION OF ORGANIC TISSUE BY LASER RADIATION

[75] Inventors: Gerhard Müller, Berlin; Peter Greve, Essingen, both of Fed. Rep. of Germany

[73] Assignee: Carl-Zeiss-Stiftung, Heidenheim, Fed. Rep. of Germany

[21] Appl. No.: 124,931

[22] PCT Filed: Feb. 3, 1987

[86] PCT No.: PCT/EP87/00053
§ 371 Date: Oct. 1, 1987
§ 102(e) Date: Oct. 1, 1987

[87] PCT Pub. No.: WO87/04632
PCT Pub. Date: Aug. 13, 1987

[30] Foreign Application Priority Data

Feb. 3, 1986 [DE] Fed. Rep. of Germany ....... 3603156

[51] Int. Cl.⁴ ............................................ A61B 17/36
[52] U.S. Cl. ................................ 128/203.1; 128/664; 128/665
[58] Field of Search ......................... 128/303.1, 12–16, 128/664, 665, 395–398; 362/32

[56] References Cited

U.S. PATENT DOCUMENTS

| 4,290,433 | 9/1981 | Alfano | 128/665 |
| 4,309,998 | 1/1982 | Rosa et al. | 128/303.1 |
| 4,336,809 | 6/1982 | Clark | 128/665 |

Primary Examiner—Léon Scott, Jr.
Attorney, Agent, or Firm—Walter Ottesen

[57] ABSTRACT

The device comprises an HeNe laser (1), which emits on a wavelength of 633 nm and a second laser (5) emitting in the near-infrared range. This second laser (5) has a continuous-wave operation and emits radiation in the 800–870 mn wavelength range, preferably on an 840 nm wavelength. An optical system (14, 15) serves to widen the beams of the two lasers (1, 5) which follow the same beam path. This system (14, 15) allows continuous adjustment of the size of the field irradiated up to a maximum diameter of the order of 30 mm. For beam switching between the lasers (1, 5) and the beam outlet opening of the device, a mirror system (11, 18) is provided which comprises an outer mirror rotatable around two axes for positioning the irradiation field.

6 Claims, 2 Drawing Sheets

DEVICE FOR THERAPEUTICAL IRRADIATION OF ORGANIC TISSUE BY LASER RADIATION

FIELD OF THE INVENTION

The present invention relates to a device for therapeutically irradiating organic tissue with easer radiation.

BACKGROUND OF THE INVENTION

Such devices have become known as so-called mid or soft lasers. They are utilized for the treatment in various areas such as in rheumatology, dermatology, neurology or in dental medicine. The treatment with laser rays is painless and causes either a warming nor a macrochemical change of the tissue. The laser radiation acts in a stimulating manner on the cell activity and activates therewith the body's own healing powers; it acts above of all antiphlogistically, antiedematous and pain relieving and is also free of any side effects.

A mid-laser is known which contains an HeNe-laser and emits a radiation having a wavelength of 633 nm. This radiation is conducted via flexible glass fibers to the location where irradiation is to occur. With this, the original polarized laser radiation is depolarized. Such lasers are preferably utilized for treating wounds.

In addition, mid-lasers are known which in addition comprise a second laser which emits a radiation of a wavelength of 904 nm. Here the rays are conducted directly to the location of the irradiation, that is, without optical elements being interposed. Because of this, such a device is most difficult to manipulate.

With these known mid-lasers, the laser beam is directed across the irradiation field in the form of a scanning raster. This has the disadvantage that the power density over this field is distributed unevenly since the power density at and near the reversal point is higher than in the regions lying therebetween.

With the known mid-lasers having a laser emitting at 904 nm, this laser is pulsed with the pulse frequency being adjustable and reaching up to approximately 5 kHz in the upper range. The semiconductor diodes utilized deliver only a low power in the timed average value which generally is at approximately 5 mW and therebelow.

SUMMARY OF THE INVENTION

It is an object of the invention to provide a device for therapeutic irradiation of organic tissue such that an improved therapeutic effectiveness is obtained at a low cost compared to known devices.

In the device according to the invention, the laser operating in the near infrared range emits radiation in the wavelength range of 800 to 870 nm, preferably at 840 nm. This radiation is supplied during continuous operation and widened to a desired diameter at the location of the irradiation by means of an optical system.

In this way, an irradiation field of adjustable magnitude is charged with an evenly distributed power density with the laser delivering a capacity of approximately 100 mW as a mean value per unit of time, the laser being advantageously configured as a GaAs-semiconductor diode.

A significant improvement of the therapeutic effect is obtained by means of the selection of the wavelength and the continuous irradiation of the laser beam. With cell metabolism of organic cells, an enzyme (from the group of flavo proteins) occurs whose absorption capacity is at the highest for a short time for a time of $<10^{-3}$ s at approximately 840 nm. This enzyme absorbs photons out of the impinging laser beam and these enzymes effect among other things a charge carrier exchange. In this way, the cell membranes become polarized and thereby stimulate the cell metabolism. In this way, the body's own healing powers are activated.

The continuous irradiation of the laser beam provides that a definite number of photons per surface unit and per time unit are available at each location of the irradiated field. In this way, an adequate number of photons are made available in the wavelength range which is optimal for absorption at every occurrence of the above-mentioned absorption condition of the enzyme which exists for a short time, so that a stimulation of the cellular exchange can occur. Since the power density of irradiation is distributed evenly over the irradiated field, the stimulating effects occur across this field in unifom distribution.

In the device according to the invention, the laser beam is guided to the irradiation field via mirrors. In this way, it is assured that the polarized radiation emitted from the HeNe-laser is not depolarized on its way to the irradiation field; that is, the radiation actually arrives there as polarized radiation. It has been shown that the closure of the wound is accelerated in this way so that the device acts to a high degree in a stimulating manner on the epithelial tissue.

The use of mirrors permits great flexibility in the guidance of the radiation so that it is simple to position the irradiation field on the body to be treated.

The device according to the invention contains an arrangement for measuring internal power which is especially advantageous. This arrangement continuously indicates the power of the emitted laser radiation and thereby makes possible a precise metering of the laser radiation impinging upon the irradiation field.

It is necessary to control the intensity of the HeNe-laser when performing therapy. For this purpose, it is advantageous in the device according to the invention to mount an LCD-plate in the beam path. The gradient of the alignment of the LCD-crystal and therewith the absorption of the polarized laser beam is controlled in an especially simple manner by means of the voltage applied to the LCD-plate.

BRIEF DESCRIPTION OF THE DRAWINGS

The invention will now be explained with reference to the drawing, wherein.

DESCRIPTION OF THE PREFERRED EMBODIMENTS OF THE INVENTION

Figure 1:
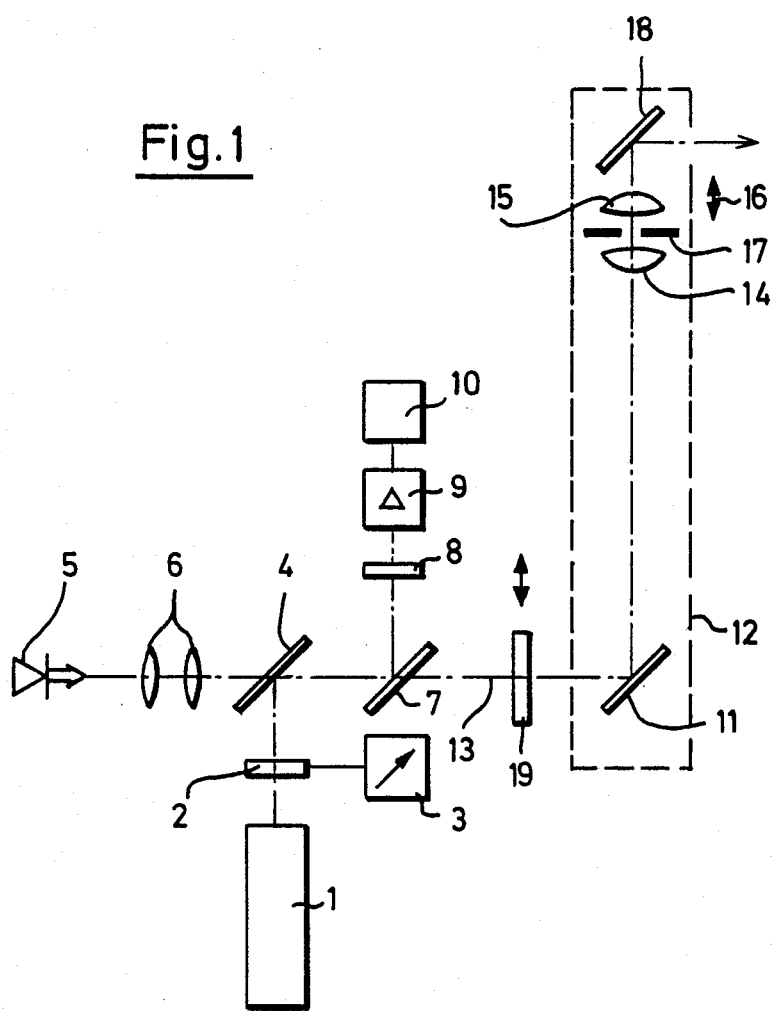
FIG. 1 is a schematic of the device according to the invention showing the components thereof and the beam path defined thereby; and, FIG. 2 is a perspective view of the device according to the invention.

In FIG. 1 (1) designates an HeNe-laser emitting at 633 nm. The polarized radiation emitted from this laser passes through an LCD-plate (2). This plate consists of a thin liquid-crystal layer which is arranged between two glass plates provided with transparent electrodes. A controllable voltage is applied between these electrodes via a control arrangement (3). The magnitude of this voltage controls the intensity of the radiation passing through the plate (2).

A dividing mirror (4) is mounted behind the LCD-plate (2) by means of which the radiation emitted from the laser diode (5) reaches the beam path. The laser diode (5) is configured as a GaAs-diode which emits 840 nm and works in continuous-wave operation. A condenser system (6) generates a parallel-beam path. The radiation emitted from lasers (1) and (2) runs behind mirror (4) coaxially over the same beam path and is influenced by the same components. A partially reflecting mirror (7) is mounted in this beam path which directs a small percentage of the impinging radiation onto a detector (8). An amplifier (9) and an indicating instrument (10) are mounted behind the detector (8). The indicating instrument (10) indicates the power in the laser beam path.

The laser beam path is deflected by a mirror (11) which is mounted in a tubular-shaped housing 12 which is rotatable about an axis coincident with the optical axis (13). An optical system for beam widening is mounted in the housing (12). The optical system in the illustrated embodiment is configured as a Kepler system made of both collective lenses (14, 15). The lens (15) is displaceable in the direction of arrow (16). A focus in the beam path is formed between lenses (14) and (15) in which a mode diaphragm (17) is mounted. The mode diaphragm (17) is configured as an iris diaphragm and is also known as a spatial filter. This diaphragm (17) serves to provide an edge defining boundary of the irradiation field whose diameter is adjusted by displacing the lens (15).

A further mirror (18) directs the laser beam out of the housing (12). This mirror is rotatable about two axes perpendicular to each other and with the aid only of an actuating member. The exemplary configuration of one such pivot mechanism is the subject matter of German utility model application G 85 35 100.8.

Further, a filter (19) is mounted in the beam path (13) so as to be pivotable in and out as indicated by the double arrow. If the irradiation with radiation of the laser (1) is to be carried out, the filter (19) is pivoted out and the entire intensity of the radiation reaches the irradiation field via the mirror (18). If the irradiation is to be carried out with the radiation of laser (5), the laser (1) remains switched on and the filter (19) is pivoted in. Only a part of the radiation at 633 nm passes through this filter. This makes possible a precise positioning of the irradiation field without initiating a therapeutic effect. Such a possibility of positioning is important since the laser (5) emits in the near infrared and its radiation is therefore not visible. The viewing field is therefore illuminated with sharp edges by the visible radiation of laser (1) and the therapeutically effective radiation of laser (5) impinges continuously and uniformly distributed precisely within this illuminated field.

The duration of the therapeutic application is controlled by means of a time switch which works directly upon the movement mechanism for the filter (19) and on the laser (5) pivots the filter (19) in when the laser (5) is switched on and vice versa.

Figure 2:
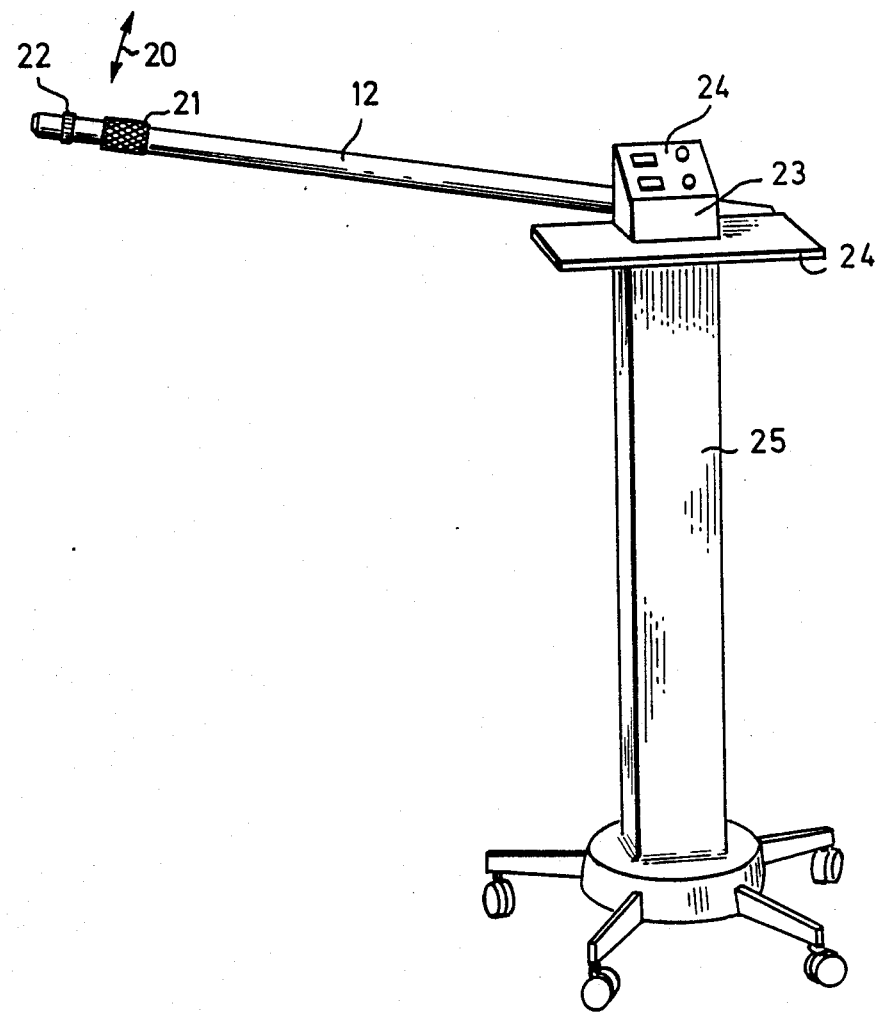

FIG. 2 shows an embodiment of the device according to the invention. One recognizes the tubular housing (12) which contains the components seen in FIG. 1. This tube is pivotable in the direction of the double arrow (20). The tube has a manipulating ring (21) for axial displacement of the lens (15), that is, to adjust the size of the irradiation field and a manipulating ring (22) for pivoting of the mirror (18). All remaining components seen in FIG. 1 are accommodated in a housing (23) which has a control field (24). The indicator (10) of the radiation intensity is mounted in this field. Further control members for pivoting the filter (19) in and out, for preselecting the irradiation duration and for actuating the lasers (1) and (5) are mounted in this field.

The housing (23) is journalled on a table (24) which is mounted on a column (25). This column is movable.

By positioning the column (25) and by pivoting the tube (12) as well as the exit mirror (18), the therapeutic laser radiation can be directed to the field to be treated of a standing, sitting or lying patient in a simple manner.

It can also be advantageous to configure the column (25) such that the table (24) is adjustable in elevation.

We claim:

1. Device for therapeutical irradiation of organic tissue with laser radiation, the apparatus comprising:
   a HeNe-laser for generating a first laser beam;
   an ancillary laser operable in continuous-wave operation in the near infrared range for emitting radiation in the wavelength range of 800 to 870 nm in the form of a second laser beam;
   optical means for guiding said first and second beams along a beam path from said lasers to the location to be irradiated;
   a housing for accommodating said optical means therein and having an exit opening through which said beams pass out of said housing and toward said location; and,
   said optical means including: beam widening means for widening said beams so as to cause the same to have a desired diameter at said location of irradiation; and, mirror means mounted in said beam path for deflecting said beams between said lasers and said exit opening.

2. The device of claim 1, said ancillary laser emitting a radiation having a wavelength of 840 nm.

3. The device of claim 2, said ancillary laser being configured as a semiconductor diode.

4. The device of claim 1, said device further comprising measuring means for measuring the power in said laser beam path.

5. The device of claim 1, said device further comprising intensity control means for adjusting the intensity of said first beam.

6. The device of claim 5, said intensity control means being an LCD-plate mounted in the path of said first beam.

* * * * *